US00PP08007P

United States Patent [19]

Kordes

[11] Patent Number: Plant 8,007

[45] Date of Patent: Oct. 20, 1992

[54] ROSE PLANT KORWILMA

[75] Inventor: Wilhelm Kordes, Sparrieshoop, Fed. Rep. of Germany

[73] Assignee: Bear Creek Gardens, Inc., Medford, Oreg.

[21] Appl. No.: 639,915

[22] Filed: Jan. 10, 1991

[51] Int. Cl.[5] ..... A01H 5/00

[52] U.S. Cl. ..... Plt./12

[58] Field of Search ..... Plt. 11, 12, 13

*Primary Examiner*—Howard J. Locker

*Attorney, Agent, or Firm*—Klarquist, Sparkman, Campbell, Leigh & Whinston

[57] ABSTRACT

A hybrid tea class rose plant having unusual red and yellow color on petals, very long vase life for a garden rose, very stiff leathery petals and many glands on peduncles, stipules, rachis and sepals.

1 Drawing Sheet

The present invention relates to a new and distinct variety of rose plant of the hybrid tea class which was originated by me by crossing the variety New Day, U.S. Plant Pat. No. 3,228, with an unnamed seedling.

The primary objective of this breeding was to produce a new rose variety having rigid petals with both red and yellow color and long vase life. The objective was substantially achieved along with other desirable improvements as evidenced by the following unique combination of characteristics which are outstanding in the new variety and which distinguish it from its parents, as well as from all other varieties of which I am aware:

1. Unusual red and yellow color of petals.
2. Very long base life for a garden rose.
3. Very stiff leathery petals.
4. Many glands on peduncles, stipules, rachis and sepals.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—New Day, U.S. Plant Pat. No. 3,228.

*Pollen parent.*—Unnamed seedling.

Classification:

*Botanical.*—*Rosa hybrida.*

*Commercial.*—Hybrid tea.

FLOWER

Observations made from specimens grown in a garden in Somis, Calif., Jun.-Sep., 1990.

Blooming habit: Recurrent.

Bud:

*Size.*—1½ inches when the petals start to unfurl.

*Form.*—Long.

*Color.*—When sepals first divide, color is Red Group 44A changing to Yellow Group 7C at the petal base. When half blown, the upper sides of the petals are Red Group 44A around the petal edges changing to Yellow 7C at the petal base; and the lower sides of the petals are Red Group 44A along the petal edges and Yellow 7C over about two-thirds of the lower petal surface.

*Sepals.*—Color: Green Group 138B. Surface texture: Covered with many fine hairs. There are three normally appendaged sepals. There are two unappendaged sepals with hairy edges and glands.

*Receptacle.*—Color: Green Group 137D. Shape: Funnel. Size: Large. Surface: Smooth.

*Peduncle.*—Length: Medium. Surface: Prickly, glandular. Color: Medium green. Strength: Stiff, erect.

Bloom:

*Size.*—Large. Average open size is 4 to 4½ inches.

*Borne.*—Singly or occasionally several together.

*Stems.*—Medium, strong (average 14 to 16").

*Form.*—When first open: High center. Permanence: Retains its form to the end, outer petals curl back.

*Petalage.*—Number of petals under normal condition: 30 to 35.

*Color.*—The upper side of the petals is Red Group 44A at the petal edges, changing to Yellow Group 7C towards the base of the petal. The reverse side of the petal is similar to the upper side but with Red Group 44A confined more to petal edge. The base of each petals is Yellow Group 7C. The major colors on the upper side are Red Group 44A and Yellow Group 7C.

*Variegations.*—None.

*Discoloration.*—No change in the general tonality at the end of the first day. By the end of the third day, the colors will fade on very bright hot days.

*Fragrance.*—Slight.

Petals:

*Texture.*—Very thick, leathery.

*Shape.*—Round.

*Form.*—Flat, tips slightly recurved.

*Arrangement.*—Imbricated. Petaloids in the center: Few.

*Persistence.*—Hang on and dry.

*Lastingness.*—On the plant: Very long (5 to 7 days). As a cut flower: Very long (7 to 10 days).

Reproductive parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: Greenish white with some reddish cast.

*Stigmas.*—Color: Greenish white.

Form: Bush.

Growth: Vigorous, upright, branching.

Foliage:

*Number of leaflets on normal mid-stem leaves.*—5.

*Size.*—Medium (5½" long×4" wide).

*Quantity.*—Abundant.

*Color.*—New foliage: Bronze-red. Old foliage: Matte green.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Rough with prickles and glands.

*Stipules.*—Medium, edges are covered with glands.

*Disease resistance.*—Susceptible to mildew and blackspot, resistant to rust under normal growing conditions at Somis, Calif.

Wood:

*New wood.*—Color: Reddish. Bark: Smooth.

*Old wood.*—Color: Green. Bark: Smooth.

Prickles:

*Quantity.*—Many on main canes from base and on laterals from main canes.

*Form.*—Medium, ¼" long, hooked downward.

*Color when young.*—Red.

Small prickles:

*Quantity.*—Many on main stalks and on laterals.

*Color.*—Brown.

I claim:

1. A new and distinct variety of rose plant of the hybrid tea class, substantially as herein shown and described, characterized particularly as to novelty by the unique combination of its stiff, leathery petals with unusual red and yellow coloration, long base life of blooms, and numerous glands on peduncles, stipules, rachis, and sepals.

* * * * *

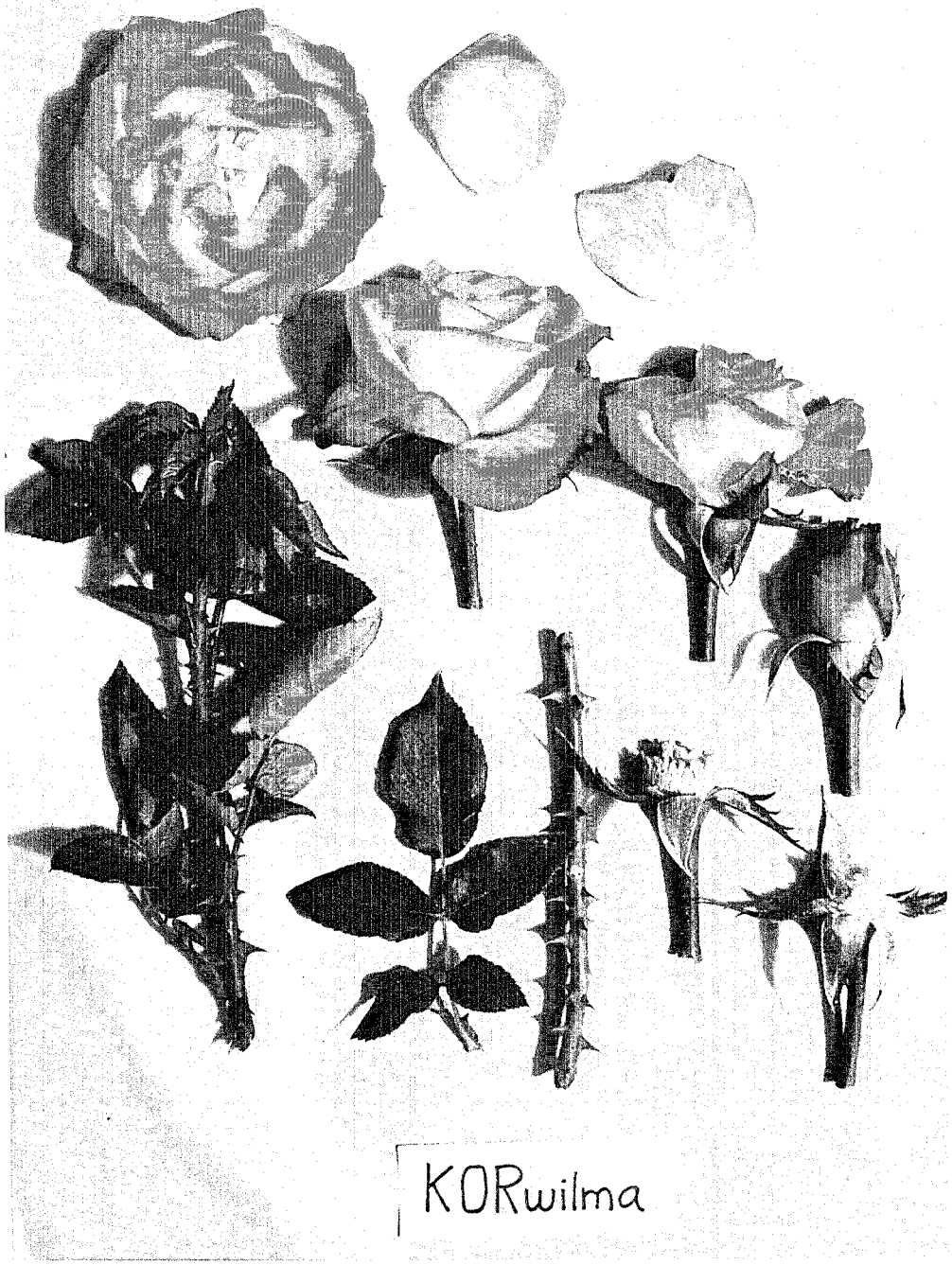
KORwilma